United States Patent
Yamabe

(10) Patent No.: US 10,272,238 B2
(45) Date of Patent: Apr. 30, 2019

(54) ELECTRODE SHEET ATTACHABLE TO LIVING TISSUES

(71) Applicant: Atsumi Yamabe, Chiba (JP)

(72) Inventor: Atsumi Yamabe, Chiba (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 15/656,015

(22) Filed: Jul. 21, 2017

(65) Prior Publication Data

US 2018/0043150 A1  Feb. 15, 2018

(30) Foreign Application Priority Data

Aug. 10, 2016  (JP) ................................. 2016-157519

(51) Int. Cl.
*A61N 1/04* (2006.01)

(52) U.S. Cl.
CPC ......... *A61N 1/0428* (2013.01); *A61N 1/0496* (2013.01)

(58) Field of Classification Search
None
See application file for complete search history.

(56) References Cited

U.S. PATENT DOCUMENTS

| | | | | |
|---|---|---|---|---|
| 7,229,556 B1* | 6/2007 | Hinds, III | ........... | A61N 1/0412 210/257.2 |
| 8,916,683 B2* | 12/2014 | Olsen | ................... | A61L 27/227 424/486 |
| 2011/0178380 A1* | 7/2011 | Chowdhury | ....... | A61B 5/14514 600/345 |
| 2014/0005269 A1* | 1/2014 | Ngwuluka | ........... | A61K 9/2077 514/567 |
| 2014/0213875 A1* | 7/2014 | Freeman | .............. | A61B 5/6839 600/386 |
| 2015/0093823 A1* | 4/2015 | Sutton | .................... | C12M 25/02 435/375 |
| 2015/0306373 A1* | 10/2015 | Bouton | ................ | A61N 1/0484 607/48 |
| 2016/0058887 A1* | 3/2016 | Ho | ................... | A61K 47/48861 424/490 |
| 2016/0331861 A1* | 11/2016 | Steele | ................... | A61L 24/001 |

FOREIGN PATENT DOCUMENTS

| | | |
|---|---|---|
| JP | 5-505757 | 8/1993 |
| JP | 2014-130718 | 7/2014 |
| JP | 2014-207987 | 11/2014 |
| JP | 2015-147856 | 8/2015 |
| WO | WO92/010235 A1 | 6/1992 |

OTHER PUBLICATIONS

Cirillo et al. Carbon Nanotubes Hybrid Hydrogels in Drug Delivery: A Perspective Review, BioMed Research International, vol. 2014 (2014), Article ID 825017, Jan. 21, 2014, 17 pages; http://dx.doi.org/10.1155/2014/825017.*

* cited by examiner

*Primary Examiner* — Brian T Gedeon
(74) *Attorney, Agent, or Firm* — Oblon, McClelland, Maier & Neustadt L.L.P.

(57) ABSTRACT

An electrode sheet attachable to living tissues is provided. The electrode sheet includes a hydrogel, a non-metallic conductive filler dispersed in the hydrogel, and a pharmaceutical or cosmetic transdermal component dispersed in the hydrogel.

18 Claims, No Drawings

ELECTRODE SHEET ATTACHABLE TO LIVING TISSUES

CROSS-REFERENCE TO RELATED APPLICATIONS

This patent application is based on and claims priority pursuant to 35 U.S.C. § 119(a) to Japanese Patent Application No. 2016-157519, filed on Aug. 10, 2016, in the Japan Patent Office, the entire disclosure of which is hereby incorporated by reference herein.

BACKGROUND

Technical Field

The present disclosure relates to an electrode sheet attachable to living tissues.

Description of the Related Art

Iontophoresis is a technology for letting a desired ingredient permeate a living tissue by the use of electrical energy. One example of iontophoresis includes a sheet in which multiple electrodes are electrically connected to each other. As the sheet is attached to the skin via the desired ingredient and a micro-current is applied to between the electrodes, the ingredient is allowed to permeate the skin.

Recently, iontophoresis has been used for improving skin permeability of pharmaceutical or cosmetic transdermal components for medical or beauty care purposes.

SUMMARY

In accordance with some embodiments of the present invention, an electrode sheet attachable to living tissues is provided. The electrode sheet includes a hydrogel, a non-metallic conductive filler dispersed in the hydrogel, and a pharmaceutical or cosmetic transdermal component dispersed in the hydrogel.

DETAILED DESCRIPTION

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In accordance with some embodiments of the present invention, an electrode sheet attachable to living tissues is provided that improves skin permeability of pharmaceutical or cosmetic components and has excellent sustained-release property.

Non-Metallic Conductive Filler

Specific preferred examples of the non-metallic conductive filler included, but are not limited to, carbon materials such as carbon nanotube, carbon black, and graphite. In particular, carbon nanotube that has high conductivity is preferable.

Usable carbon nanotubes include both monolayer carbon nanotubes and multilayer carbon nanotubes. For improving flexibility and skin following property of the electrode, the carbon nanotube is preferably thin and soft as much as possible.

Carbon nanotube is a fibrous material having specific thickness and length. In particular, carbon nanotubes, the fibers and/or fiber bundles of which can form a three-dimensional conductive network even in the hydrogel, are preferably used. As the conductive network is formed, conductivity of the electrode sheet and skin permeability of the transdermal component are improved and excellent sustained-release property is provided.

Preferably, the carbon nanotube has a diameter of from 1 to 500 nm, more preferably from 1 to 200 nm, and most preferably from 1 to 50 nm.

Preferably, the carbon nanotube is as large as possible in length, for reducing contact resistance between carbon nanotube molecules and improving conductivity.

Preferably, the content rate of the non-metallic conductive filler in the electrode sheet is in the range of from 0.01% to 5% by mass, more preferably from 0.3% to 3% by mass. When the content rate of the non-metallic conductive filler is in the range of from 0.01% to 5% by mass, dispersibility in the hydrogel is good. When the content rate of the non-metallic conductive filler is less than 0.01% by mass, the resistance of the electrode sheet becomes higher and skin permeability of the transdermal component becomes lower. When the content rate of the non-metallic conductive filler is in excess of 5% by mass, dispersibility of the non-metallic conductive filler in the hydrogel deteriorates, thereby causing aggregation of the non-metallic conductive filler.

Preferably, the electrode sheet has an electric resistance in the range of from $10\Omega$ to $100\ k\Omega$, more preferably from 30 to $200\Omega$.

Hydrogel

Specific examples of the hydrogel include, but are not limited to: gels containing natural polymers, such as agar, gelatin, agarose, xanthane gum, gellan gum, sclerotium gum, gum arabic, gum tragacanth, gum karaya, cellulose gum, tamarind gum, guar gum, locust bean gum, glucomannan, chitosan, carrageenan, quince seed, galactan, mannan, starch, dextrin, curdlan, casein, pectin, collagen, fibrin, peptide, chondroitin sulfates (e.g., sodium chondroitin sulfate), hyaluronic acid (mucopolysaccharide), hyaluronates (e.g., sodium hyaluronate), alginic acid, alginates (e.g., sodium alginate, calcium alginate), and derivatives thereof: gels containing cellulose derivatives (e.g., methyl cellulose, hydroxymethyl cellulose, hydroxyethyl cellulose, hydroxypropyl cellulose, hydroxypropyl methyl cellulose, carboxymethyl cellulose) and salts thereof; gels containing polyacrylic acid or polymethacrylic acid (e.g., polyacrylic acid, polymethacrylic acid, alkyl copolymers of acrylic acid and methacrylic acid) and salts thereof; gels containing synthetic polymers such as polyvinyl alcohol, polyhydroxyethyl methacrylate, polyacrylamide, poly(N-isopropylacrylamide), polyvinyl pyrrolidone, polystyrene sulfonic acid, polyethylene glycol, carboxyvinyl polymer, alkyl-modified carboxyvinyl polymer, maleic anhydride copolymer, polyalkylene-oxide-based resin, N-vinylacetamide cross-linked body, acrylamide cross-linked body, and starch-acrylate graft copolymer cross-lined product; silicone hydrogel; interpenetrating-network-structure or semi-interpenetrating-network-structure hydrogel; and combinations thereof. In particular, for improving load resistance and biocompatibility, gels containing collagen and/or glucomannan, gels containing carboxymethyl cellulose and/or carboxymethyl cellulose sodium, gels containing polyacrylic acid and/or sodium polyacrylate, and interpenetrating-network-structure of semi-interpenetrating-network-structure hydrogel are preferable. Commercially available hydrogels can also be used, such as AQUAJOINT (a polyacrylic gel) available from Nissan Chemical Industries, Ltd.

The hydrogel accounts for 90% by volume or more of the electrode sheet.

Transdermal Components

Examples of the transdermal component include the following pharmaceutical transdermal components.

Examples of pharmaceutical transdermal components having an anti-aging effect include, but are not limited to, uric acid, glutathione, melatonine, polyphenol, melanoidin, astaxanthin, kinetin, epigallocatechin gallate, coenzyme Q10, vitamins, superoxide dismutase, mannitol, quercetin, catechin and derivatives thereof, rutin and derivatives thereof, moutan bark extracts, YASHAJITU extracts, melissa (lemon balm) extracts, siraitia grosvenorii (monk fruit) extracts, dibutylhydroxytoluene, and butylhydroxyanisol.

Examples of pharmaceutical transdermal components having a whitening effect include whitening agents and anti-inflammatory agents. Whitening agents have a function of preventing the occurrence of skin darkening caused by suntan and flecks and freckles caused by pigmentation. Specific examples of whitening agents include, but are not limited to arbutin, ellagic acid, linoleic acid, vitamin C and derivatives thereof, kojic acid, tranexamic acid, placenta extracts, chamomile extracts, glycyrrhiza extracts, rose fruit extracts, scutellaria root extracts, seaweed extracts, sophora root extracts, suberect spatholobus stem extracts, acanthopanax bark extracts, rice bran extracts, wheat germ extracts, asiasarum root extracts, cragaegus fruit extracts, cassia mimosoides L. extracts, white lily extracts, peony root extracts, inula flower extracts, soy bean extracts, tea extracts, molasses extracts, ampelopsis japonica extracts, grape extracts, hop extracts, rosa rugosa extracts, chaenomeles fruit extracts, and strawberry geranium extracts. Anti-inflammatory agents have a function of suppressing the occurrence of skin burning sensation or inflammations such as red spots caused by suntan. Specific examples of anti-inflammatory agents include, but are not limited to, sulfur and derivatives thereof, glycyrrhizic acid and derivatives thereof, glycyrrhetic acid and derivatives thereof, althaea extracts, Angelica keiskei extracts, arnica extracts, artemisia capillaris flower extracts, nettle extracts, phellodendron bark extracts, hypericum erectum extracts, chamomile extracts, lonicera flower extracts, watercress extracts, comfrey extracts, salvia extracts, lithospermum root extracts, perilla extracts, white birch extracts, and gentian extracts.

Specific examples of cosmetic transdermal components having a peeling and brightening effect include, but are not limited to, α-hydroxylic acid, salicylic acid, sulfur, and urea.

Examples of pharmaceutical transdermal components having a slimming effect include, but are not limited to, those having a blood circulation promoting effect, such as plant extracts (e.g., ginger, capsicum tincture, sophora root), carbonic acid gas, and vitamin E and derivatives thereof.

Examples of pharmaceutical transdermal components having a moisturizing effect include, but are not limited to, proteins (e.g., elastin, keratin) and derivatives, hydrolyzates, and salts thereof, amino acids (e.g., glycine, serine, aspartic acid, glutamic acid, arginine, theanine) and derivatives thereof, sorbitol, erythritol, trehalose, inositol, glucose, sucrose and derivatives thereof, dextrin and derivatives thereof, sugars (e.g., honey), D-panthenol and derivatives thereof, sodium lactate, sodium pyrrolidone carbonate, sodium hyaluronate, mucopolysaccharide, urea, phospholipid, ceramide, coptis rhizome extracts, calamus (sweet flag) extracts, rehmannia root extracts, cnidium rhizome extracts, common mallow extracts, thyme extracts, houttuynia cordata extracts, hamamelis extracts, tilia miqueliane extracts, marronnier (horse chestnut) extracts, and quince extracts.

Examples of pharmaceutical transdermal components having a hair restoring effect include, but are not limited to, phospholipid polymer, hydrolyzed collagen, 18-MEA, hydrolyzed wheat protein, hydrolyzed rice protein, phosphate compounds, and inositol.

Examples of pharmaceutical transdermal components having a hair growing effect include, but are not limited to, isopropyl methyl phenol, ginkgo biloba extract, L-menthol, carpronium chloride, diphenhydramine hydrochloride, polygonum root, dipotassium glycyrrhizate, salicylic acid, dialkyl monoamine derivatives, ginger, cepharanthine, cnidium rhizome, swertia herb, panax rhizome, panax ginseng, capsicum tincture, Japanese angelica root, trehalose, nicotinic acid/nicotinic acid amide, vitamin E (tocopherol), hinokitiol, placenta extracts, and pentadecanic acid glyceride.

Examples of pharmaceutical transdermal components having a skin conditioning effect include, but are not limited to, those for improving barrier function and healing damaged skin, such as ceramides, cholesterols, amine derivatives, caffeine, cockscomb extracts, shell extracts, royal jelly, silk protein and decompositions products and derivatives thereof, lactoferrin and decomposition products thereof, chondroitin sulfate, mucopolysaccharides (e.g., hyaluroic acid) and salts thereof, collagen, yeast extracts, lactic acid bacteria extracts, bifidobacterium extracts, fermentation methabolism extracts, ginkgo biloba extracts, barley extracts, swertia herb extracts, jujube extracts, ginseng extracts, arnica extracts, turmeric extracts, eucalyptus extracts, typha latifolia, saponaria officinalis extracts, rosemary extracts, glycolic acid, citric acid, lactic acid, malic acid, tartaric acid, and succinic acid.

Examples of pharmaceutical transdermal components having a relaxing effect include, but are not limited to, lavender, rosemary, sandalwood, orris, bitter orange, cypress, and orange oil.

Examples of the transdermal component further include cosmetic transdermal components, such as skin lotion, milky lotion, beauty essence, skin cream, cream for facial pack, massage cream, cleansing cream, cleansing gel, face washing foam, sunscreen, hair styling gel, shampoo, body shampoo, hair setting gel, fragrance, and hair dye.

Each of the above transdermal components may be used alone or in combination with others.

The transdermal component may be in a particular dosage form. For example, a hydrophilic transdermal component may be dispersed or dissolved in a water-based medium, and a lipophilic transdermal component may be dispersed or dissolved in an oil-based medium.

The dosage form may be of a water-based type, solubilization type, multilayer type, oil-in-water type, water-in-oil type, oil-based type, water-in-oil-in-water type, or oil-in-water-in-oil type, but is not limited thereto. Both hydrophilic and lipophilic transdermal components can effectively exert their function by the use of liposome or vesicle. The transdermal component may be encapsulated by a block copolymer having both hydrophobic and hydrophilic regions to be in the form of a transdermal medicine or cosmetic composition containing polymer micelles. Such a dosage form is particularly advantageous for transdermal components having a large molecular weight, such as hyaluronic acid and collagen.

Preferably, the content rate of the transdermal component in the electrode sheet is in the range of from 1% to 10% by mass, more preferably from 3% to 7% by mass.

The electrode sheet may be produced by an ordinary method including the processes of, for example, preliminarily stirring all constituents with a stirrer, homogenizing the constituents with a high-pressure jet-mill homogenizer, dispersing the non-metallic conductive filler and the transdermal component in the hydrogel, and forming the obtained hydrogel-based material into a sheet. The size of the electrode sheet is determined depending on the position on a living tissue where the electrode sheet is to be attached and/or the type of the transdermal component.

The electrode sheet may be equipped with a lead electrode plate for passing a current disposed outside the hydrogel. The electrode plate may be made of any conductive material. Examples of the conductive material include a conductive tape.

The electrode sheet contains multiple electrodes for applying a micro-current to a living tissue. According to on embodiment, an electric circuit including multiple electrodes may be formed on one surface of the electrode sheet by a conventional circuit forming technology. According to another embodiment, the electrode sheet may be disposed on a previously-formed electric circuit including multiple electrodes.

Examples of the conventional circuit forming technology include a flexible printed board forming technology, but are not limited thereto. The electrodes may comprise gold, platinum, silver, or copper. A substrate on which the electrodes are formed may comprise a sheet-like insulating substrate, such as commercially-available polyimide films and polyethylene naphthalate films. A current source may be either a direct of alternating current source. Examples of the current source include conventional devices for use in iontophoresis, but are not limited thereto. In addition, devices capable of applying a current to living tissues, such as low-frequency therapy equipments may be used as the current source.

The living tissues to which the electrode sheet is to be attached include the skin of face, finger, arm, or body and keratin-containing tissues consisting primarily of keratin, such as hair, nail, lip, and oral cavity inner surface, but are not limited thereto. The electrode sheet may be attached to various tissues forming exterior and interior surfaces of living bodies.

In a case in which the electrode sheet is attached to the face, an intensive medicine administration for a particular position may be achieved by adjusting the wiring.

EXAMPLES

Further understanding can be obtained by reference to certain specific examples which are provided herein for the purpose of illustration only and are not intended to be limiting.

Evaluation Methods

Resistance Value

Four randomly-selected positions on each electrode sheet were subjected to a measurement of resistance value at room temperature using an instrument LORESTA GP MCP-T610 available from Mitsubishi Chemical Analytech Co., Ltd. The measured values were averaged. The area and thickness of the electrode sheet were 1 $cm^2$ and 0.5 cm, respectively.

Permeability of Transdermal Component

Each electrode sheet was attached to an agarose gel, and a current of 0.45 mA/$cm^2$ was applied thereto at 25° C.

The permeation distance of the transdermal component (calcein) was measured from a cross-section of the agarose gel.

A: The moving distance of calcein was in the range of from 0.15 to 0.2 mm after a lapse of 30 minutes. Excellent sustained-release property as cosmetics.

B: The moving distance of calcein was 0.10 mm or greater but less than 0.15 mm after a lapse of 30 minutes.

C: The moving distance of calcein was 0.05 mm or greater but less than 0.10 mm after a lapse of 30 minutes.

D: The moving distance of calcein was less than 0.05 mm after a lapse of 30 minutes.

Dispersibility

Dispersibility of the non-metallic conductive filler in the hydrogel was evaluated by visual observation. Specifically, the hydrogel was spread into a transparent-film-like shape and visually observed to determine presence or absence of aggregation.

Example 1

Preparation of Electrode Sheet

First, 3.6 g of a commercially-available carbon nanotube ("CNT") (multi-walled carbon nanotube ("MWNT") having a length of 10 μm and a diameter of 5 nm), 0.0062 g of calcein (available from Tokyo Chemical Industry Co., Ltd.) serving as a pharmaceutical agent, and 6 g of AQUAJOINT (available from Nissan Chemical Industries, Ltd.) were mixed, and stirred with a magnetic stirrer at a revolution of 700 rpm for 2 minutes. The obtained mixture was treated with a high-pressure jet-mill homogenizer (NANO JET PUL® JN10 available from JOKOH CO., LTD., 60 MPa), thus obtaining a hydrogel composition. The CNT-containing hydrogel composition thus obtained was adhered onto an electrode that had been formed by ink-jetting silver on a polyethylene film. Thus, an electrode sheet was prepared. The area and thickness of the electrode sheet were 1 $cm^2$ and 0.5 cm, respectively.

Iontophoresis Device

As a current source for an iontophoresis device, a current voltage generator 6241A (available from ADC CORPORATION) was used. The iontophoresis device comprises an electrode terminal for connecting to an electrode disposed on the electrode sheet, and the current voltage generator to which the electrode terminal connects via an electrode terminal connecting part.

Example 2

The procedure in Example 1 was repeated except for changing the addition amount of the non-metallic conductive filler as described in Table 1, thus obtaining an electrode sheet.

Example 3

The procedure in Example 1 was repeated except for replacing the non-metallic conductive filler with acetylene black ("CB") (a powdery material DENKA BLACK available from Denka Company Limited), thus obtaining an electrode sheet.

Example 4

The procedure in Example 3 was repeated except for changing the addition amount of the acetylene black ("CS")

(a powdery material DENKA BLACK available from Denka Company Limited) as described in Table 1, thus obtaining an electrode sheet.

Example 5

The procedure in Example 1 was repeated except for replacing the AQUAJOINT with a polyvinyl alcohol, thus obtaining an electrode sheet. The polyvinyl alcohol was a commercially-available product PVA-217 from Kuraray Co., Ltd. Specifically, 10% of the polyvinyl alcohol and 1% of borax were dissolved or mixed in water and the same amount of the pharmaceutical agent was introduced thereto. The resultant was applied onto an electrode that had been prepared by forming a wiring on a polyethylene film, and let dry naturally.

Comparative Example 1

The procedure in Example 1 was repeated except for adding no non-metallic conductive filler, thus obtaining an electrode sheet.

Comparative Example 2

The electrode sheet was obtained from a gelatin GEL01 (available from Zero C Seven, Inc.), generally used for electrodermal response, without using either the non-metallic conductive filler or AQUAJOINT.

The results were presented in Table 1.

TABLE 1

| | Example 1 | Example 2 | Example 3 | Example 4 | Example 5 | Comp. Example 1 | Comp. Example 2 |
|---|---|---|---|---|---|---|---|
| Pharmaceutical Agent (Calcein) (g) | 0.0062 | 0.0062 | 0.0062 | 0.0062 | 0.0062 | 0.0062 | 0.0062 |
| Type of Non-metallic Conductive Filler | CNT | CNT | CB | CB | CNT | — | — |
| Addition Amount of Non-metallic Conductive Filler (% by mass) | 0.37 | 3.00 | 0.37 | 3.00 | 0.37 | — | — |
| Resistance Value ($\Omega$) | 21 | 20 | 85 | 40 | 56 | 10M | 6M |
| Skin Permeability of Transdermal Component | A | A | C | B | B | D | D |
| Dispersibility (Aggregation) | No | No | No | No | No | No | No |

It is clear from Table 1 that the electrode sheets according to some embodiments of the present invention, in each of which the non-metallic conductive filler and the pharmaceutical or cosmetic transdermal component are dispersed in the hydrogel, provide high skin permeability of the transdermal component and excellent sustained-release property. By contrast, in Comparative Examples 1 and 2, either skin permeability of the transdermal component or sustained-release property is poor, because no non-metallic conductive filler is dispersed in the hydrogel.

Numerous additional modifications and variations are possible in light of the above teachings. It is therefore to be understood that, within the scope of the above teachings, the present disclosure may be practiced otherwise than as specifically described herein. With some embodiments having thus been described, it will be obvious that the same may be varied in many ways. Such variations are not to be regarded as a departure from the scope of the present disclosure and appended claims, and all such modifications are intended to be included within the scope of the present disclosure and appended claims.

The invention claimed is:

1. An electrode sheet attachable to living tissues, comprising:
    a hydrogel;
    a non-metallic conductive filler dispersed in the hydrogel; and
    a pharmaceutical or cosmetic transdermal component dispersed in the hydrogel,
    wherein the electrode sheet has an electric resistance in the range of from 10$\Omega$ to 100 k$\Omega$, and the hydrogel accounts for 90% by volume or more of the electrode sheet.

2. The electrode sheet of claim 1, wherein the non-metallic conductive filler comprises carbon nanotube.

3. The electrode sheet of claim 2, wherein the carbon nanotube form a three-dimensional conductive network in the hydrogel.

4. The electrode sheet of claim 2, wherein the electrode sheet is prepared by mixing the hydrogel, the non-metallic conductive filler, and the pharmaceutical or cosmetic transdermal component together.

5. The electrode sheet of claim 1, wherein a content rate of the non-metallic conductive filler in the electrode sheet ranges from 0.01% to 5% by mass.

6. The electrode sheet of claim 5, wherein the non-metallic conductive filler comprises carbon black.

7. The electrode sheet of claim 1, wherein the non-metallic conductive filler comprises carbon black.

8. The electrode sheet of claim 7, wherein the electrode sheet is prepared by mixing the hydrogel, the non-metallic conductive filler, and the pharmaceutical or cosmetic transdermal component together.

9. The electrode sheet of claim 1, wherein the electrode sheet is prepared by mixing the hydrogel, the non-metallic conductive filler, and the pharmaceutical or cosmetic transdermal component together.

10. An electrode sheet attachable to living tissues, comprising:
    a hydrogel;

a non-metallic conductive filler dispersed in the hydrogel; and a pharmaceutical or cosmetic transdermal component dispersed in the hydrogel, wherein the electrode sheet has an electric resistance in the range of from 30 to 200Ω, and the hydrogel accounts for 90% by volume or more of the electrode sheet.

11. The electrode sheet of claim 10, wherein the non-metallic conductive filler comprises carbon nanotube.

12. The electrode sheet of claim 11, wherein the carbon nanotube form a three-dimensional conductive network in the hydrogel.

13. The electrode sheet of claim 11, wherein the electrode sheet is prepared by mixing the hydrogel, the non-metallic conductive filler, and the pharmaceutical or cosmetic transdermal component together.

14. The electrode sheet of claim 10, wherein a content rate of the non-metallic conductive filler in the electrode sheet ranges from 0.01% to 5% by mass.

15. The electrode sheet of claim 14, wherein the non-metallic conductive filler comprises carbon black.

16. The electrode sheet of claim 10, wherein the non-metallic conductive filler comprises carbon black.

17. The electrode sheet of claim 16, wherein the electrode sheet is prepared by mixing the hydrogel, the non-metallic conductive filler, and the pharmaceutical or cosmetic transdermal component together.

18. The electrode sheet of claim 10, wherein the electrode sheet is prepared by mixing the hydrogel, the non-metallic conductive filler, and the pharmaceutical or cosmetic transdermal component together.

\* \* \* \* \*